United States Patent [19]

Kishita et al.

[11] Patent Number: 5,300,613

[45] Date of Patent: Apr. 5, 1994

[54] FLUORINE-CONTAINING ORGANOSILICON COMPOUNDS

[75] Inventors: Hirofumi Kishita; Shinichi Sato; Takashi Matsuda, all of Annaka, Japan

[73] Assignee: Shin-Etsu Chemical Co., Ltd., Tokyo, Japan

[21] Appl. No.: 69,847

[22] Filed: Jun. 1, 1993

[30] Foreign Application Priority Data

Jun. 2, 1992 [JP] Japan ................... 4-167025
Jun. 17, 1992 [JP] Japan ................... 4-183167

[51] Int. Cl.$^5$ ................. C08G 77/24; C08G 77/26; C07F 7/16
[52] U.S. Cl. ................. 528/26; 528/28; 528/31; 528/42; 556/419; 556/445; 556/436
[58] Field of Search ............ 556/419, 445, 436; 528/42, 28, 26, 31

[56] References Cited

U.S. PATENT DOCUMENTS

| | | | |
|---|---|---|---|
| 3,271,362 | 9/1966 | Chalk et al. | 528/42 |
| 3,542,830 | 11/1970 | Kim et al. | 528/42 |
| 4,094,911 | 6/1978 | Mitsch et al. | 556/419 |
| 4,608,270 | 8/1986 | Varaprath | 427/35 |
| 4,742,177 | 5/1988 | Yamamoto et al. | 556/419 |
| 4,900,474 | 2/1990 | Terae et al. | 252/358 |
| 5,208,312 | 5/1993 | Boutevin et al. | 528/28 |

FOREIGN PATENT DOCUMENTS 0328397 8/1989 European Pat. Off. .

*Primary Examiner*—John C. Bleutge
*Assistant Examiner*—Margaret W. Glass
*Attorney, Agent, or Firm*—Oblon, Spivak, McClelland, Maier & Neustadt

[57] ABSTRACT

Fluorine-containing organosilicon compounds having the following general formula:

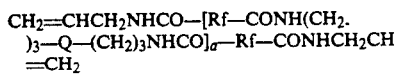

wherein a is an integer of 1 or above, Rf is a divalent perfluoropolyether group, and Rf is a divalent cyclosiloxane group containing an unsubstituted or substituted monovalent hydrocarbon group without an aliphatically unsaturated bond. The compounds are of use as a starting material in synthesizing rubbers or mold release agents which are high in such properties as solvent resistance, chemical resistance and the like.

3 Claims, 5 Drawing Sheets

FLUORINE-CONTAINING ORGANOSILICON COMPOUNDS

BACKGROUND OF THE INVENTION

1. Field of the Invention

The present invention relates to new fluorine-containing organosilicon compounds which have not appeared in the literature.

2. Description of the Prior Art

Fluorine-containing organosilicon compounds are known to be useful as starting materials in preparation of ingredients for producing rubber materials or mold release agents which have high resistance to solvents and chemicals.

Recently, in addition, the requirements that rubbers or mold release agents should meet in regard to solvent resistance, chemical resistance, mold release property and so forth have come to be extremely high.

SUMMARY OF THE INVENTION

It is accordingly an object of the present invention to provide new fluorine-containing organosilicon compounds which are highly suited to use as a starting material in synthesis of a component material for forming rubber materials or mold release agents which are high in the properties as above-described.

According to the present invention, there is provided a fluorine-containing organosilicon compound which has the following general formula (1):

$$CH_2\!\!=\!\!CHCH_2NHCO\!-\![Rf\!-\!CONH(CH_2)_3\!-\!Q\!-\!(CH_2)_3NHCO]_a\!-\!Rf\!-\!CONHCH_2CH\!\!=\!\!CH \quad (1)$$

wherein a is an integer of 1 or above, Rf is a divalent fluorine-containing organic group having the following general formula (2):

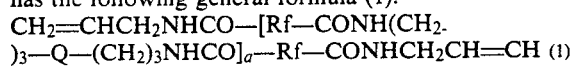

wherein X is a fluorine atom or CF$_3$ group, l is an integer form 0 to 8, k and m are each an integer from 1 to 20, and j and n are each an integer of 0 or 1; and Q is a siloxane group having one of the following general formulas (3), ((4) and (5):

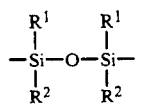

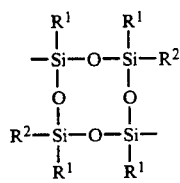

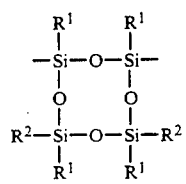

wherein R$^1$ and R$^2$ are each an unsubstituted or substituted monovalent hydrocarbon group without an aliphatically unsaturated group.

DETAILED DESCRIPTION OF PREFERRED EMBODIMENTS

Figure 1:
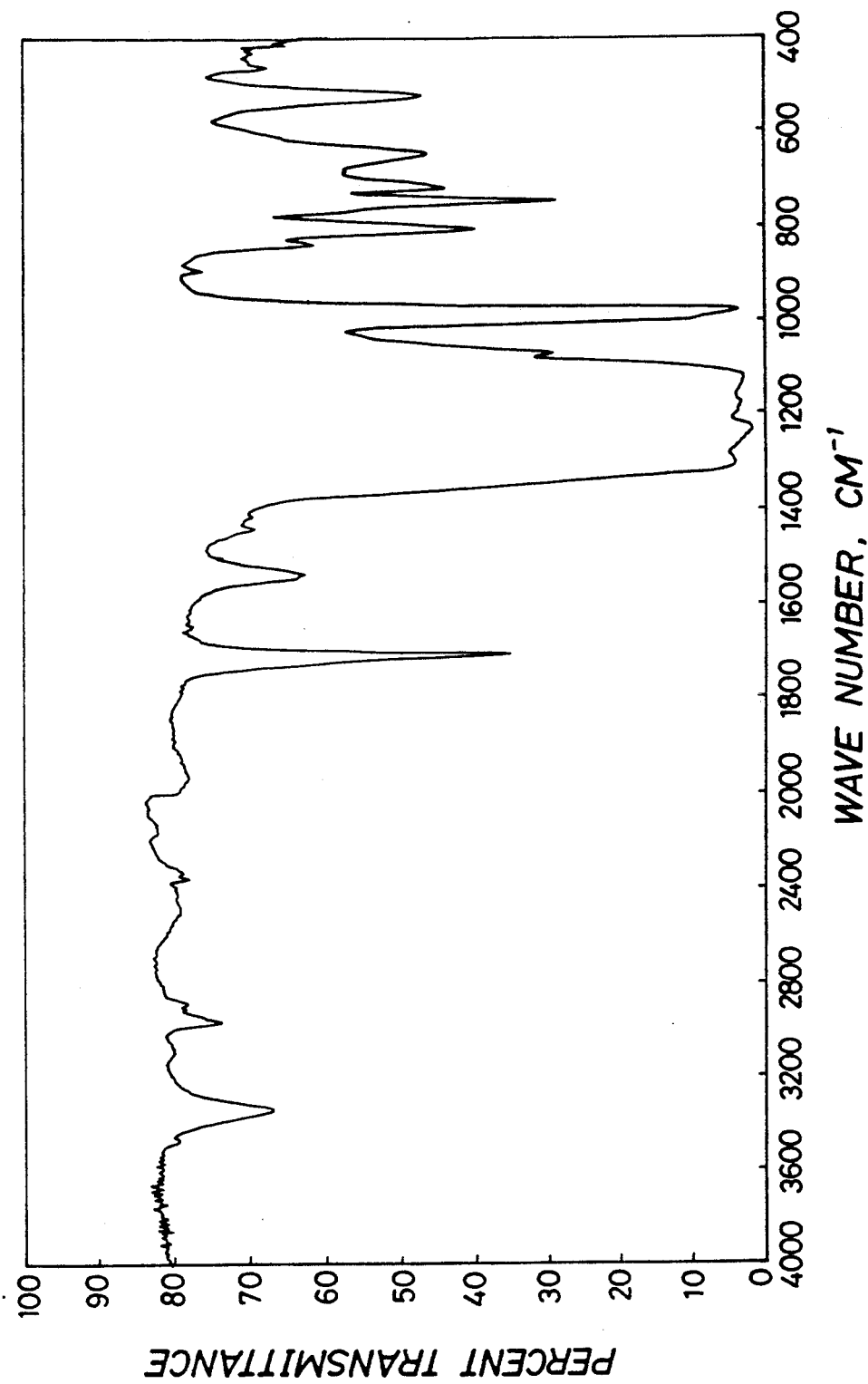
FIGS. 1 to 5 are diagrams showing IR charts for the fluorine-containing organosilicon compounds of the present invention which are synthesized in Examples 1 to 5, respectively.

In the above general formula (1) of the fluorine-containing organosilicon compounds according to the present invention, the divalent fluorine-containing organic group Rf has the general formula (2) above, and typical but not limitative examples of the group Rf include the followings:

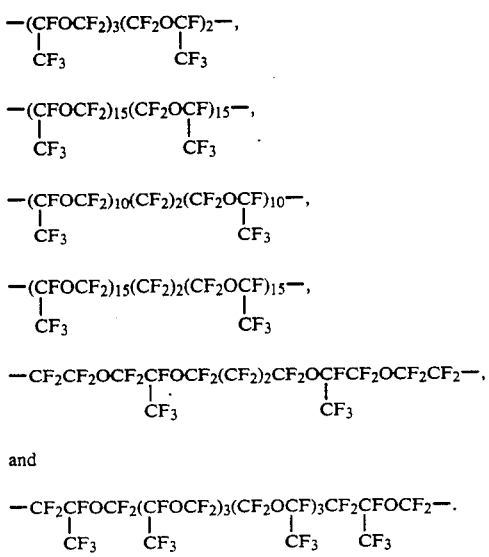

and $$-CF_2CFOCF_2(CFOCF_2)_3(CF_2OCF)_3CF_2CFOCF_2-.$$
$$\quad\ |\qquad\ \ |\qquad\qquad\ |\qquad\ \ |$$
$$\ \ CF_3\quad\ CF_3\qquad\ CF_3\quad\ CF_3$$

The divalent siloxane group Q has one of the above general formulas (3), (4) and (5). In these formulas (3) to (5), R$^1$ and R$^2$ may be the same or different from each other and are each an unsubstituted or substituted monovalent hydrocarbon group without an aliphatically unsaturated bond. The monovalent groups R$^1$ and R$^2$ include, for example, alkyl groups such as methyl, ethyl, propyl, butyl, hexyl and the like; aryl groups such as phenyl and the like; aralkyl groups such as benzyl, phenylethyl and the like; and groups derived from these groups by substituting a part of their hydrogen atoms with halogen, such as, for instance, 3,3,3-trifluoropropyl, and the like. Among these monovalent groups, particularly preferred are alkyl and 3,3,3-trifluoropropyl. Typical examples of the siloxane group Q are as follows.

The siloxane groups Q that have the above general formula (3) include, for example, the followings:

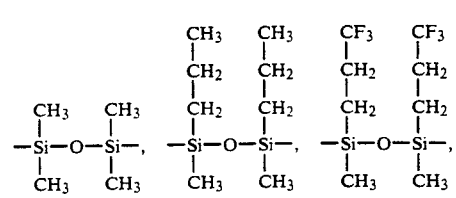

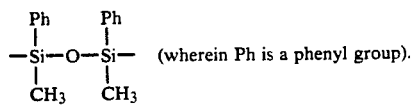 (wherein Ph is a phenyl group).

The siloxane groups Q that have the above general formula (4) include, as typical examples there, the followings:

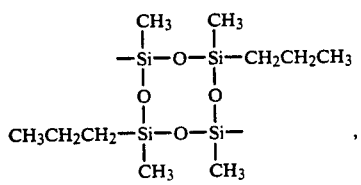,

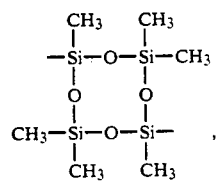,

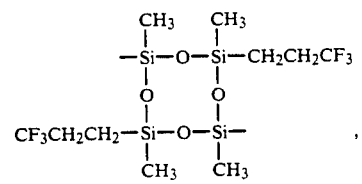,

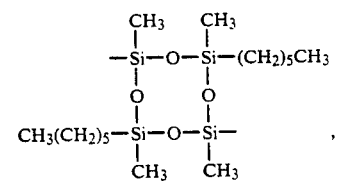, and

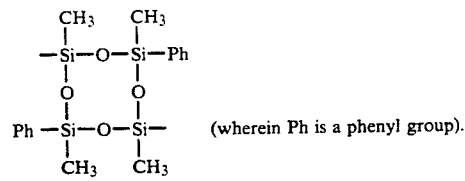 (wherein Ph is a phenyl group).

The siloxane groups Q that have the above general formula (5) include, for example, the following groups:

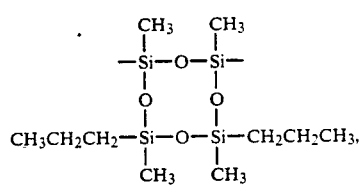,

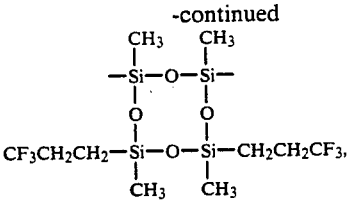, and

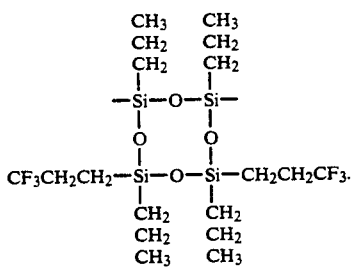

METHOD OF PREPARATION

The fluorine-containing organosilicon compounds according to the present invention can be prepared, for example, by reacting a compound having allyl group at both ends represented by the following formula (6):

$$CH_2=CHCH_2NHCO-Rf-CONHCH_2CH=CH_2 \quad (6)$$

wherein Rf is the same as defined above, and a siloxane of the following general formula (7):

$$H-Q-H$$

wherein Q is the same as defined above, in the presence of an addition reaction catalyst.

In the reaction, the allyl-terminated compound of the formula (6) is preferably used in an excess amount relative to the siloxane of the formula (7). It is particularly preferable to use these reactants in amounts such that the mole ratio of the amount of the allyl-terminated compound to the siloxane is in the range from 1 (exclusive) to 2 (inclusive). If the amount of the allyl-terminated compound is increased, a polymer having a relatively smaller molecular weight is formed upon the reaction. Where the amount of the allyl-terminated compound is decreased, on the other hand, a polymer with a greater molecular weight is obtained.

The addition reaction is carried out ordinarily at a temperature of from 50° to 150° C., and preferably from 80 to 120° C.

Catalysts which can be used as the addition reaction catalyst include the elements of the Group VIII of the periodic table and compounds thereof, for example, chloroplatinic acid, alcohol-modified chloroplatinic acid (Refer to U.S. Pat. No. 3,220,972), chloroplatinic acidolefin complex (Refer to U.S. Pat. Nos. 3,159,601, 3,159,662 and 3,775,452), platinum black or palladium supported on alumina, silica, carbon or other carrier, rhodium-olefin complex, chlorotris(triphenylphosphine)rhodium (Wilkinson's catalyst), and the like. These complexes are preferably used in the form of solutions in alcohol-, ketone-, ether- or hydrocarbon-based solvents.

Alternatively, the fluorine-containing organosilicon compounds of the present invention can also be prepared by reacting a compound having ethyl ester group at both ends represented by the following formula (8):

$$CH_3CH_2OOC-Rf-COOCH_2CH_3 \quad (8)$$

with a compound having amino group at both ends represented by the following formula (9):

$$H_2N-(CH_2)_3-Q-(CH_2)_3-NH_2 \quad (9)$$

wherein Q is the same as above, at room temperature to 80° C., then further reacting allylamine therewith, followed by removing the ethyl alcohol by-produced.

In the reaction, the ethyl ester group-terminated compound of the formula (8) is preferably used in an excess amount relative to the amino compound of the formula (9). It is particularly preferable to use these reactants in amounts such that the mole ratio of the ethyl ester compound to the amino compound ranges from 1 (exclusive) to 2 (inclusive). An increase in the amount of the ethyl ester group-terminated compound results in the formation of a polymer of a relatively smaller molecular weight, whereas a decrease in the amount leads to the formation of a polymer of a greater molecular weight. This preparation method is especially suited to the synthesis of the inventive fluorine-containing organosilicon compounds of the type in which the siloxane group Q is represented by the above general formula (3).

The fluorine-containing organosilicon compounds of the present invention obtained in the manner as described above can be used for a variety of applications.

For instance, the fluorine-containing organosilicon compounds of the present invention, when reacted with a compound having at least three hydrosilyl groups in its molecule in the presence of an addition reaction catalyst, give elastomers. Such elastomers have a high fluorine content and, therefore, high resistance to solvents and chemicals. Furthermore, the elastomers have a low surface energy and, hence, good release properties and water repellency. Therefore, the elastomers can be used as materials for producing sealants, moldings, extrusions, coating materials and other various applications.

EXAMPLES

The present invention will now be described in more detail below, with reference to working examples thereof. In the examples below, the viscosity is given in values measured at 25° C.

EXAMPLE 1

A 200-ml four-necked separable flask equipped with stirring rod, thermometer, Dimroth condenser and dropping funnel was charged with 51.5 g of a compound having allyl group at both ends (viscosity: 2930 cP) of the following formula:

$$CH_2=CHCH_2NHCO-(CFOCF_2)_{15}(CF_2OCF)_{15}-CONHCH_2CH=CH_2$$
$$\quad\quad\quad\quad\quad\quad\quad\quad | \quad\quad\quad\quad\quad\quad |$$
$$\quad\quad\quad\quad\quad\quad\quad\quad CF_3 \quad\quad\quad\quad\quad CF_2$$

and 50.0 g of m-xylene hexafluoride. The contents of the flask was heated to 90° C. with stirring, and 0.05 g of a 2% solution of chloroplatinic acid in isopropyl alcohol was added thereto. Then, 1.01 g of a siloxane of the following formula:

$$\begin{array}{ccc} CH_3 & & CH_3 \\ | & & | \\ H-Si-O-Si-H \\ | & & | \\ CH_3 & & CH_3 \end{array}$$

was added dropwise through the dropping funnel, to allow reaction to take place. After the dropwise addition, the reaction mixture was matured. The maturing was continued until the disappearance of the siloxane was confirmed on a gas chromatograph, upon which the reaction mixture was cooled to room temperature and admixed with 1.5 g of active carbon, followed by stirring for 2 hours. Then, the reaction mixture was subjected to pressure filtration through a filter plate. The filtrate thus obtained was vacuum stripped at 200° C. and 3 mmHg, to yield 48.7 g of a pale yellow transparent liquid.

The viscosity of the liquid obtained was measured to be 9120 cP.

An NMR analysis of the liquid gave a peak due to Si—CH$_3$ at 0.23 ppm.

Further, the liquid was subjected to IR spectroscopic analysis and elemental analysis, giving the following results.

| IR analysis: IR chart is shown in FIG. 1. | |
|---|---|
| 1100–1300 cm$^{-1}$ | C—F |
| 1705 cm$^{-1}$ | C=O |
| 3340 cm$^{-1}$ | N—H |

| | Elemental analysis: | | | | | |
|---|---|---|---|---|---|---|
| | C | O | H | N | F | Si |
| Calcd. (%): | 23.1 | 10.0 | 0.4 | 0.5 | 65.2 | 0.8 |
| Found (%): | 22.9 | 9.8 | 0.5 | 0.7 | 65.5 | 0.6 |

Besides, vinyl group content of the liquid obtained above was determined to be 0.0097 mol/100 g.

From the above results it was confirmed that the pale yellow transparent liquid product was a polymer having the following structural formula:

$$CH_2=CHCH_2NHCO-[Rf-CONH(CH_2)_3-Q-(CH_2)_3NHCO]_3-Rf-CONHCH_2CH=CH_2$$

$$Rf: \; -(CFOCF_2)_{15}(CF_2OCF)_{15}- \quad\quad Q: \; \begin{array}{c} CH_3 \quad CH_3 \\ | \quad\quad | \\ -Si-O-Si- \\ | \quad\quad | \\ CH_3 \quad CH_3 \end{array}$$
$$\quad\quad | \quad\quad\quad\quad\quad |$$
$$\quad\quad CF_3 \quad\quad\quad\quad CF_3$$

EXAMPLE 2

A 200-ml four-necked separable flask equipped with stirring rod, thermometer, Domroth condenser and dropping funnel was charged with 52.2 g of a compound having allyl group at both ends (viscosity: 3050 c:) of the following formula:

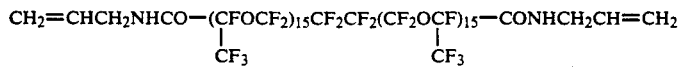

and 50.0 g of m-xylene hexafluoride. The contents of the flask was heated to 90° C. with stirring, and 0.05 g of a 2% solution of chloroplatinic acid in isopropyl alcohol was added thereto. Then, 2.24 g of a siloxane of the following formula:

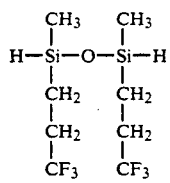

was added dropwise through the dropping funnel, to allow reaction to take place. After the dropwise addition, the reaction mixture was matured. The maturing was continued until the disappearance of the siloxane was confirmed on a gas chromatograph, upon which the reaction mixture was cooled to room temperature and admixed with 1.5 g of active carbon, followed by stirring for 2 hours. Then, the reaction mixture was subjected to pressure filtration through a filter plate. The filtrate thus obtained was vacuum stripped at 200° C. and 3 mmHg, to yield 49.2 g of a pale yellow transparent liquid.

The viscosity of the liquid obtained was measured to be 10,400 cP.

An NMR analysis of the liquid gave a peak due to Si—CH$_3$ at 0.27 ppm.

Further, the liquid was subjected to IR spectroscopic analysis and elemental analysis, giving the following results.

Figure 2:
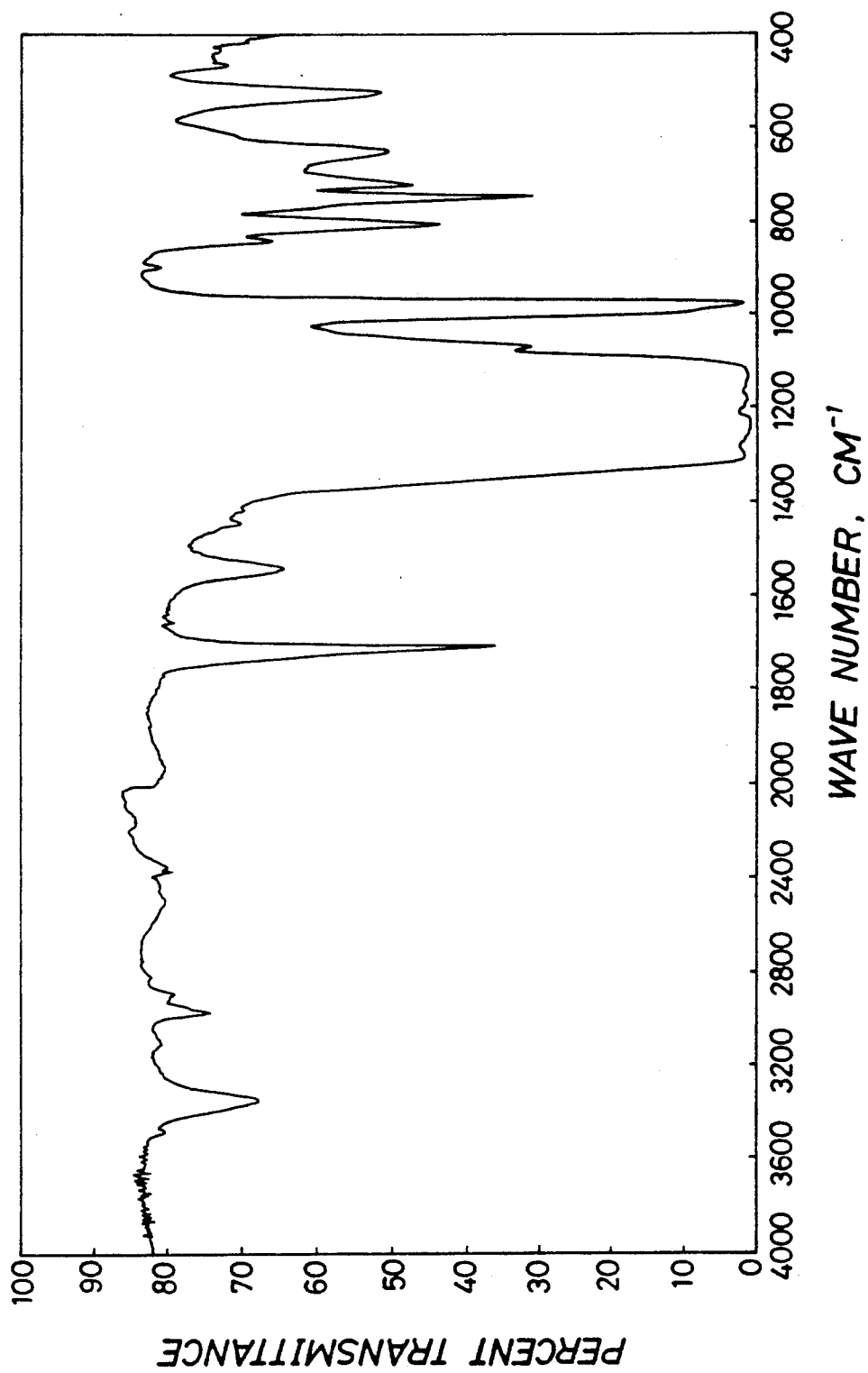

| IR analysis: IR chart is shown in FIG. 2. | |
|---|---|
| 1100-1300 cm$^{-1}$ | C—F |
| 1705 cm$^{-1}$ | C=O |
| 3340 cm$^{-1}$ | N—H |

| Elemental analysis: | | | | | | |
|---|---|---|---|---|---|---|
| | C | O | H | N | F | Si |
| Calcd. (%): | 23.2 | 9.6 | 0.4 | 0.5 | 65.2 | 0.8 |
| Found (%): | 23.5 | 9.4 | 0.5 | 0.5 | 65.1 | 1.0 |

Besides, vinyl group content of the liquid obtained above was determined to be 0.0095 mol/100 g.

From the above results it was confirmed that the pale yellow transparent liquid product was a polymer having the following structural formula:

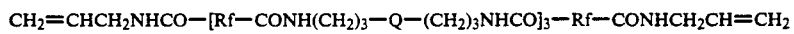

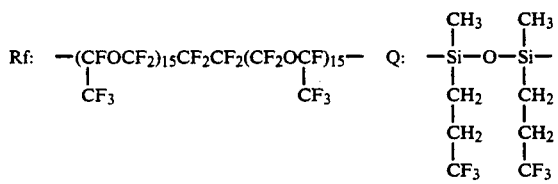

EXAMPLE 3

A 200-ml four-necked separable flask equipped with stirring rod, thermometer, Dimroth condenser and dropping funnel was charged with 51.3 g of a compound having ethyl ester group at both ends (viscosity: 3250 cP) of the following formula:

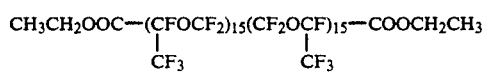

and 50.0 g of m-xylene hexafluoride. The contents of the flask was heated to 50° C. with stirring, and 1.86 g of a siloxane having amino group at both ends with the following formula:

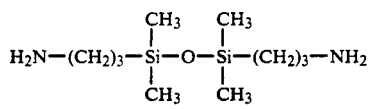

was added dropwise through the dropping funnel, to allow reaction to take place. After the dropwise addition, the reaction mixture was matured. After the disappearance of the aminosiloxane was confirmed on a gas chromatograph, 0.48 g of allylamine was added dropwise to the reaction mixture, followed by further maturing for an additional 2 hour period. Then, the reaction mixture was subjected to vacuum stripping at 200° C. and 3 mmHg to distill off low-boiling-point compounds such as ethanol having been by-produced. Thereafter, the reaction mixture thus treated was cooled to room temperature and admixed with 1.5 g of active carbon, followed by stirring for 2 hours. The resulting reaction mixture was subjected to pressure filtration through a filter plate, whereupon 49.5 g of a pale yellow transparent liquid was obtained.

The viscosity of the liquid obtained was measured to be 11,200 cP.

An NMR analysis of the liquid gave a peak due to Si—CH$_3$ at 0.23 ppm.

Further, the liquid was subjected to IR spectroscopic analysis and elemental analysis, giving the following results.

Figure 3:
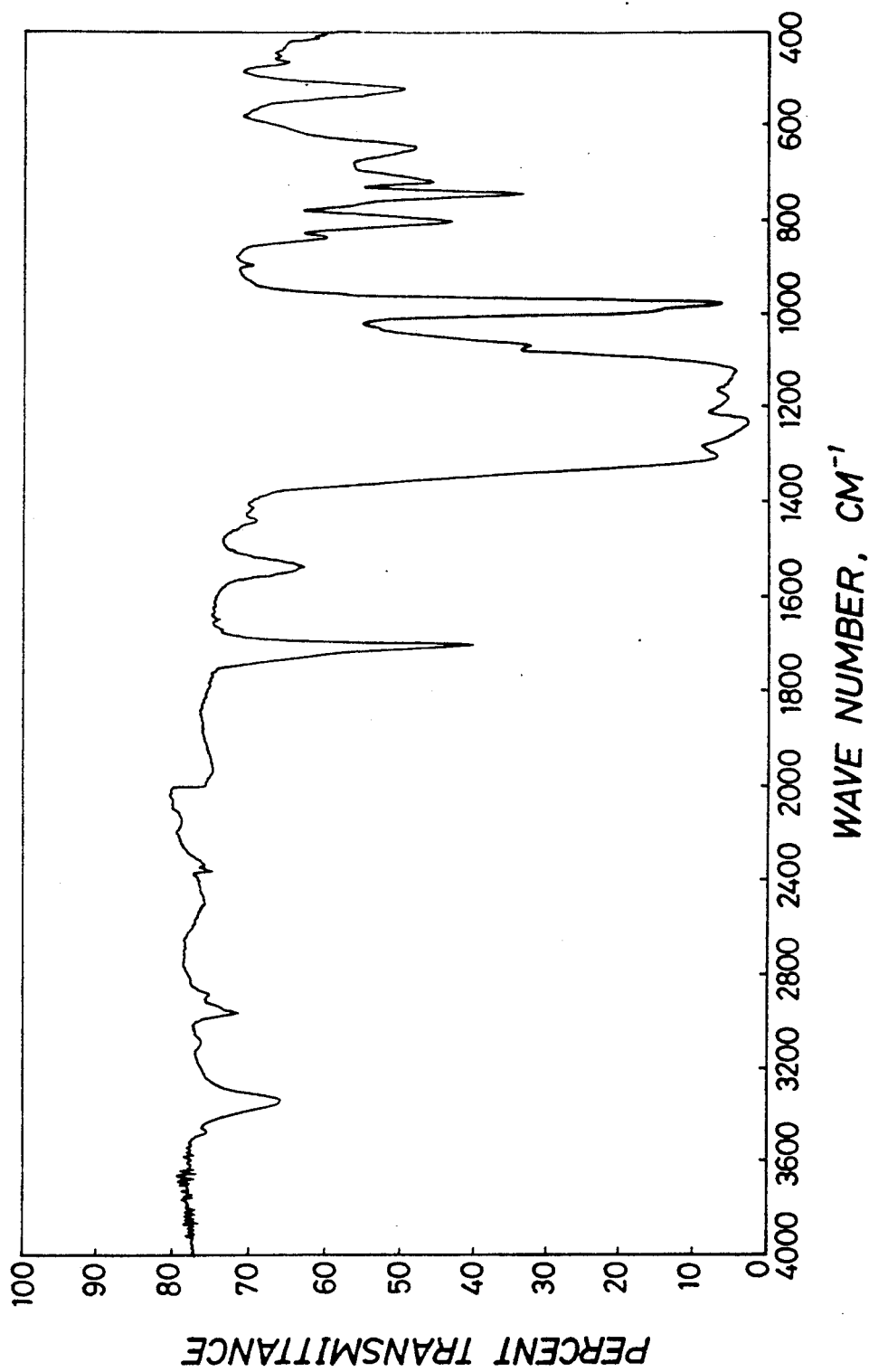

| IR analysis: IR chart is shown in FIG. 3. | |
|---|---|
| 1100-1300 cm$^{-1}$ | C—F |

-continued

| IR analysis: IR chart is shown in FIG. 3. | |
|---|---|
| 1705 cm$^{-1}$ | C=O |
| 3330 cm$^{-1}$ | N—H |

| Elemental analysis: | | | | | | |
|---|---|---|---|---|---|---|
| | C | O | H | N | F | Si |
| Calcd. (%): | 23.1 | 10.0 | 0.4 | 0.5 | 65.2 | 0.8 |
| Found (%): | 23.0 | 9.6 | 0.4 | 0.5 | 65.4 | 1.0 |

Besides, vinyl group content of the liquid obtained above was determined to be 0.0091 mol/100 g.

From the above results it was confirmed that the pale yellow transparent liquid product was a polymer having the following structural formula:

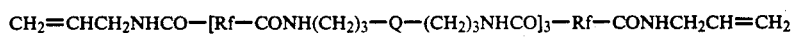

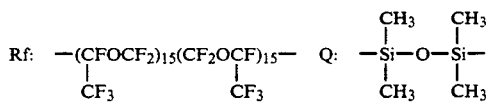

EXAMPLE 4

A 200-ml four-necked separable flask equipped with stirring rod, thermometer, Dimroth condenser and dropping funnel was charged with 51.5 g of a compound having allyl group at both ends (viscosity: 2930 cP) of the following formula:

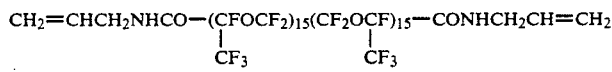

and 50.0 g of m-xylene hexafluoride. The contents of the flask was heated to 90° C. with stirring, and 0.05 g of a 2% solution of chloroplatinic acid in isopropyl alcohol was added thereto. Then, 2.16 g of a cyclotetrasiloxane of the following formula:

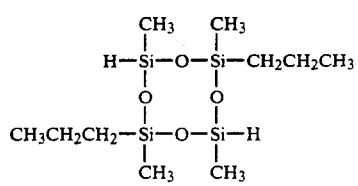

was added dropwise through the dropping funnel, to allow reaction to take place. After the dropwise addition, the reaction mixture was matured. The maturing was continued until the disappearance of the cyclotetrasiloxane was confirmed on a gas chromatograph, upon which the reaction mixture was cooled to room temperature and admixed with 1.5 g of active carbon, followed by stirring for 2 hours. Then, the reaction mixture was subjected to pressure filtration through a filter plate. The filtrate thus obtained was vacuum stripped at 200° C. and 3 mmHg, to yield 49.3 g of a pale yellow transparent liquid.

The viscosity of the liquid obtained was measured to be 8880 cP.

Figure 4:
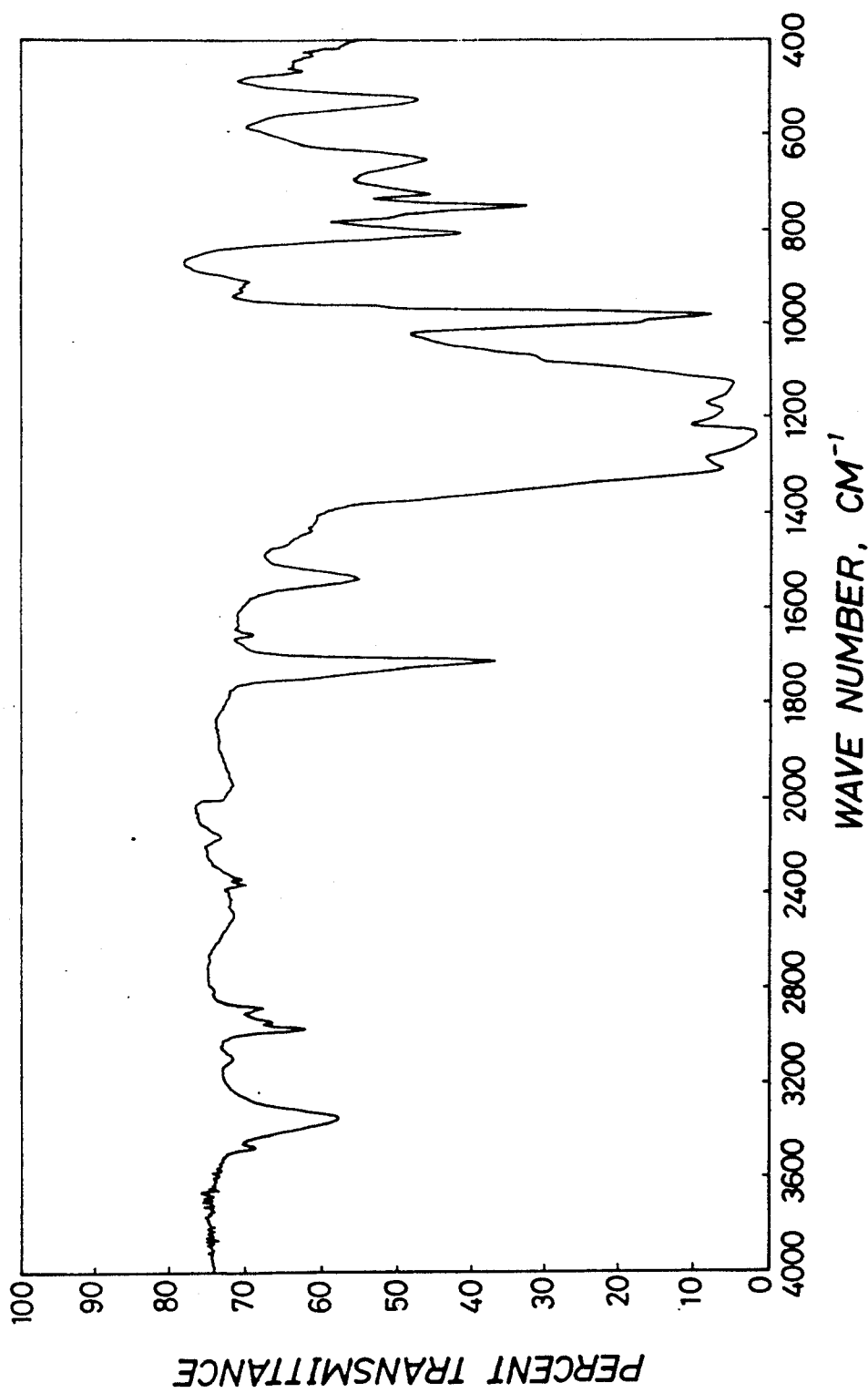

Further, the liquid was subjected to IR spectroscopic analysis, showing IR absorption as below (IR chart is shown in FIG. 4).

| 1100-1300 cm$^{-1}$ | C—F |
|---|---|
| 1705 cm$^{-1}$ | C=O |
| 3350 cm$^{-1}$ | N—H |

Besides, vinyl group content of the liquid obtained above was determined to be 0.0013 mol/100 g.

From the above results it was confirmed that the pale yellow transparent liquid product was a polymer having the following structural formula:

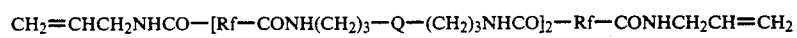

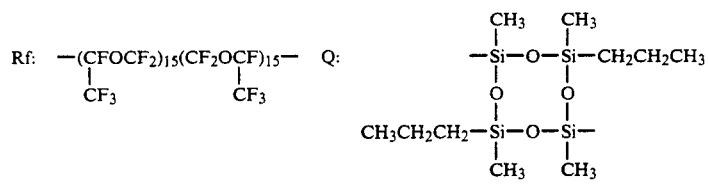

EXAMPLE 5

A 200ml four-necked separable flask equipped with stirring rod, thermometer, Dimroth condenser and dropping funnel was charged with 52.2 g of a compound having allyl group at both ends (viscosity: 3050 cP) of the following formula:

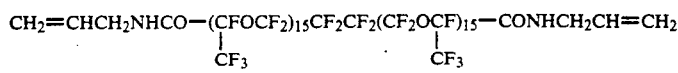

and 50.0 g of m-xylene hexafluoride. The contents of the flask was heated to 90° C. with stirring, and 0.05 g of a 2% solution of chloroplatinic acid in isopropyl alcohol was added thereto. Then, 2.88 of a cyclotetrasiloxane of the following formula:

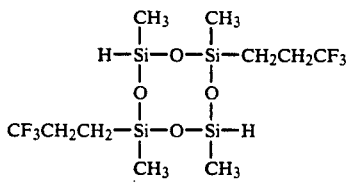

was added dropwise through the dropping funnel, to allow reaction to take place. After the dropwise addition, the reaction mixture was matured. The maturing was continued until the disappearance of the cyclotetrasiloxane was confirmed on a gas chromatograph, upon which the reaction mixture was cooled to room temperature and admixed with 1.5 g of active carbon, followed by stirring for 2 hours. Then, the reaction mixture was subjected to pressure filtration through a filter plate. The filtrate thus obtained was vacuum stripped at 200° C. and 3 mmHg, to yield 50.1 g of a pale yellow transparent liquid.

The viscosity of the liquid obtained was measured to be 9230 c:.

Figure 5:
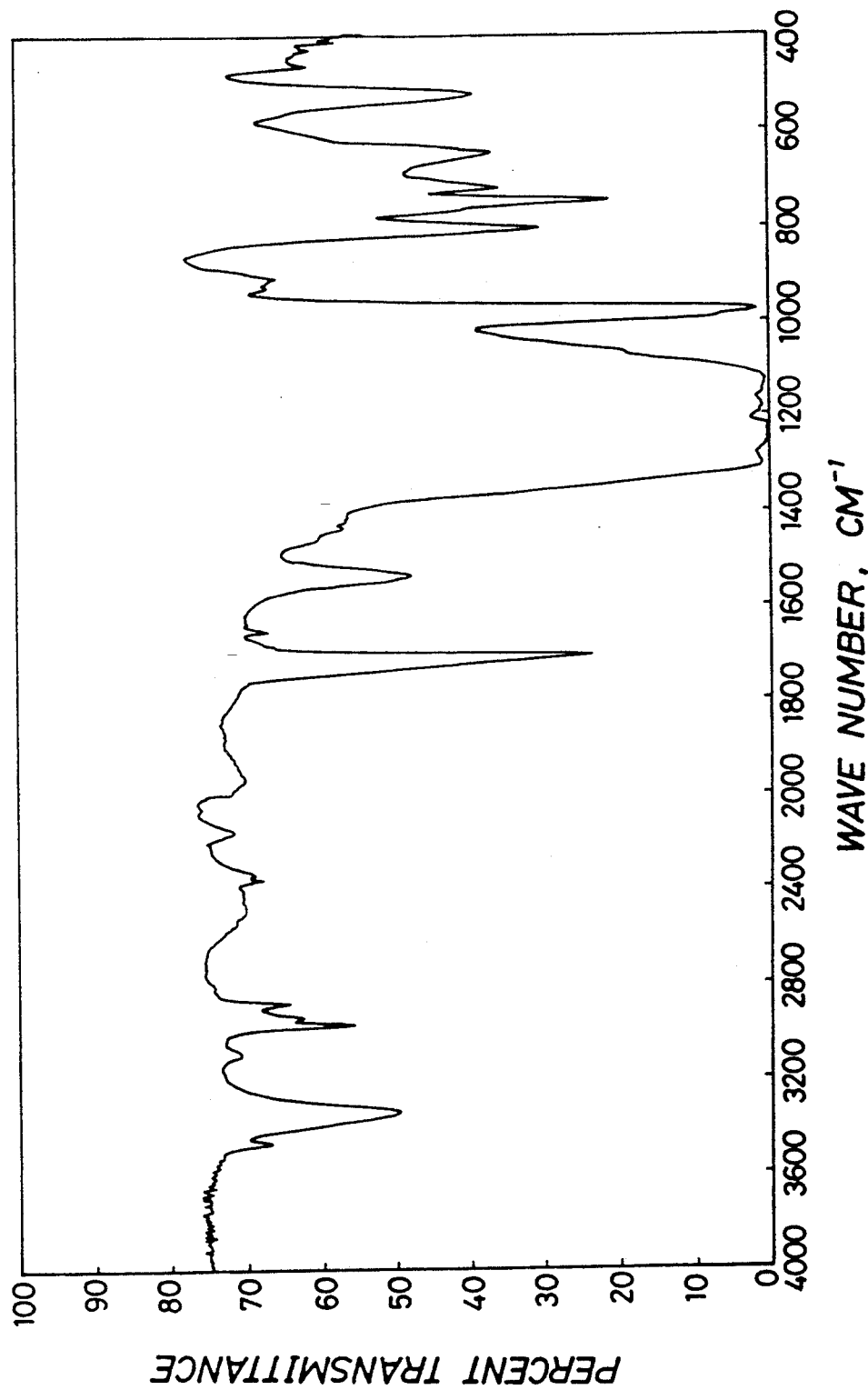

Further, the liquid was subjected to IR spectroscopic analysis, showing IR absorption as below (IR chart is shown in FIG. 5).

| 1100–1300 cm$^{-1}$ | C—F |
|---|---|
| 1705 cm$^{-1}$ | C=O |
| 3340 cm$^{-1}$ | N—H |

Besides, vinyl group content of the liquid obtained above was determined to be 0.0012 mol/100 g.

From the above results it was confirmed that the pale yellow transparent liquid product was a polymer having the following structural formula:

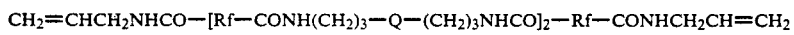

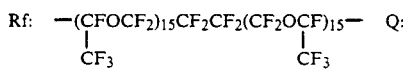 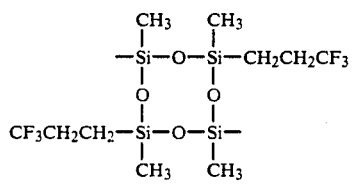

We claim:

1. A fluorine-containing organosilicon compound which has the following general formula (1):

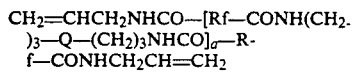 (1)

wherein a is an integer of 1 or above, Rf is a divalent fluorine-containing organic group having the following general formula (2):

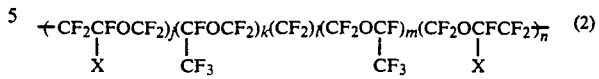 (2)

wherein X is a fluorine atom or CF$_3$ group, l is an integer from 0 to 8, k and m are each an integer from 1 to 20, and j and n are each an integer of 0 or 1; and Q is a siloxane group having one of the following general formulas (3), (4) and (5):

 (3)

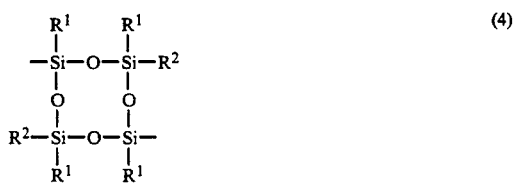 (4)

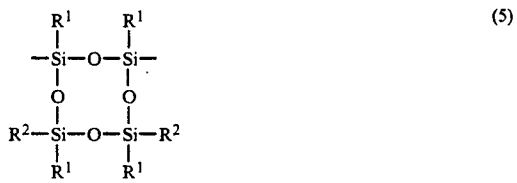 (5)

wherein R$^1$ and R$^2$ are each an unsubstituted or substituted monovalent hydrocarbon group without an aliphatically unsaturated group.

2. The compound of claim 1, wherein in the general formulas (3) to (5), the groups R$^1$ and R$^2$ are each a group selected from the group consisting of alkyl, aryl and aralkyl groups whose hydrogen atom may be substituted by a halogen atom.

3. The compound of claim 2, wherein the groups R$^1$ and R$^2$ are each a group selected from the group consisting of alkyl, phenyl and 3,3,3-trifluoropropyl groups.

* * * * *